Aug. 13, 1935. A. F. J. BAUR Plant Pat. 133
CARNATION
Filed April 4, 1935
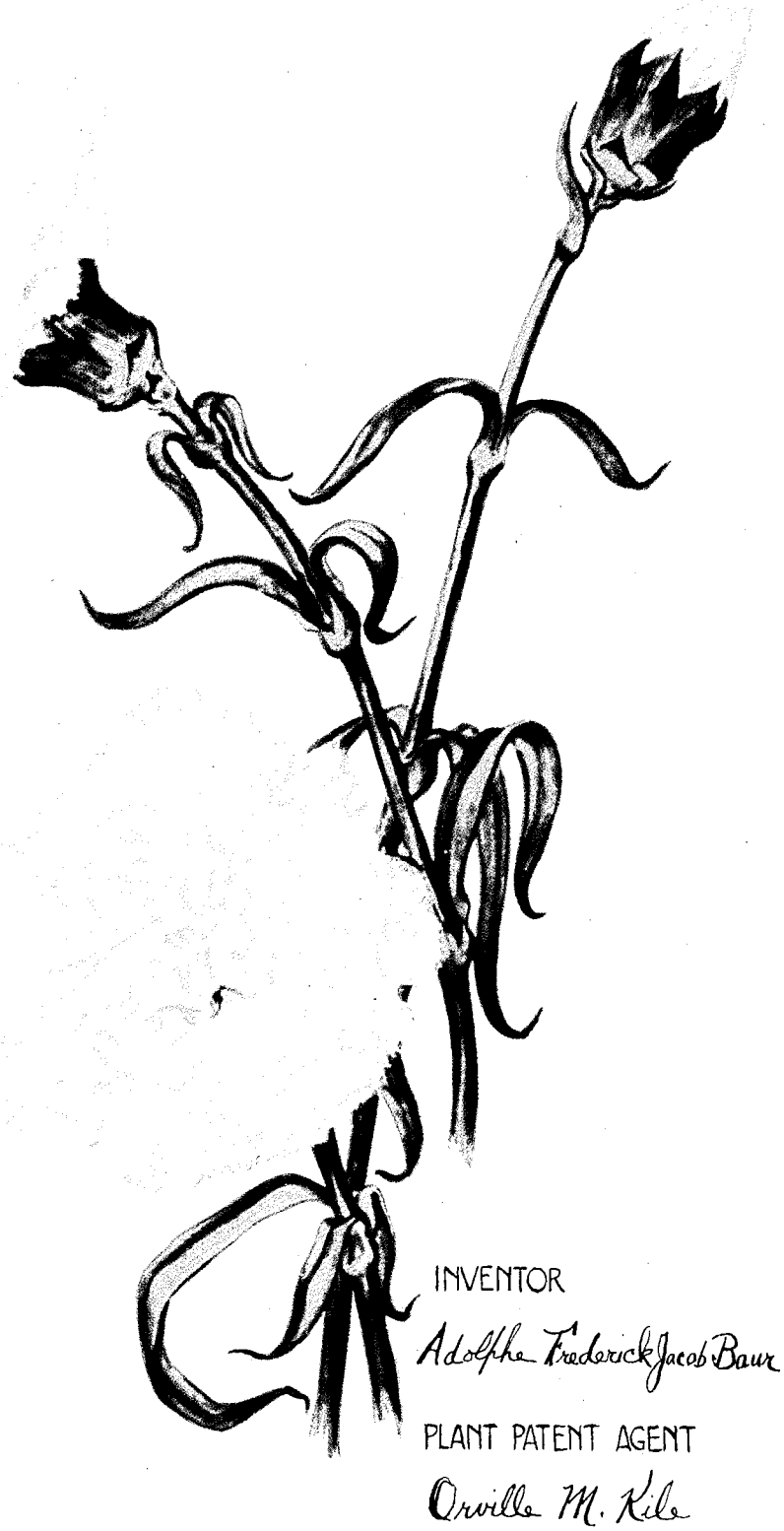

Patented Aug. 13, 1935 Plant Pat. 133

UNITED STATES PATENT OFFICE

133

CARNATION

Adolphe Frederick Jacob Baur, Indianapolis, Ind., assignor to Baur-Steinkamp and Company, Incorporated, Indianapolis, Ind.

Application April 4, 1935, Serial No. 14,711

1 Claim. (Cl. 47—60)

My present invention relates to improvements in fragrant, medium pink carnations of the type ordinarily known as perpetual blooming or greenhouse forcing carnations. The object of my invention is to provide a medium pink carnation of the type mentioned having a fuller and more perfect form of flower richer in salmon tones of color; having stronger stems and better calyx than in somewhat similar varieties; having foliage of a distinctive and pleasing color; and having the quality of earlier blooming and greater productiveness.

This new variety is the result of careful plant breeding operations carried on by myself and associates. This seedling first bloomed in 1929 and has since been thoroughly tested.

The original illustrations show in full natural color and approximately natural size, a side view and a front view of the blossom and an opening bud, as well as stems and leaves. It must be understood, however, that the artist's colors cannot always quite duplicate nature's colors.

The following is a more detailed description of this new variety of carnation:

The plant is a vigorous grower of more than average height. During the height of the season (about January 30 in the vicinity of Indianapolis, Indiana) this variety attains a normal height of about three feet.

The plant is not grassy in form but provides an ample supply of foliage.

Apparently this variety is resistant to diseases.

An important feature of this variety is its ability to come into flower at an early age and to produce heavily.

Cuttings root easily and rooted plants stand transplanting well.

The foliage is a distinctive feature of this variety in that it has a fresh blue-green appearance not found in the older standard varieties in the midwinter season.

The leaves are short to medium in length and of medium width. Not inclined to curl readily. Nodal joints prominent.

The stems are rather heavy, being considerably heavier than those of somewhat similar medium pink varieties.

*Calyx.*—Relatively short and wide and not given to bursting—an important feature in a flower as full as this variety. Bracts at the base of the calyx are well developed.

*Buds.*—Rather short and wide.

*Flowers.*—Large, full and well formed. When fully opened flowers measure 3½ to 3¾ inches across the top. The flower has a close well-filled center.

In late December the average number of petals is 45 to 50.

Each individual petal is irregularly serrated on its upper edge and has a moderately crinkled surface.

Ridgeway's Color Standards and Nomenclature is of little value in attempting to describe or identify the color of this carnation. There simply is no color or shade in the standards that resembles the color of this carnation. The nearest approach is "rose color" (Plate XII), but there is an admixture of salmon or carrot red color which materially modifies the effect. The outer edges of some of the petals also show a slight purplish cast in certain lights.

While the color effect at a glance is solid or uniform, close inspection shows that the color is not laid on solidly. The color is broken by light streaks and elongated blotches which while not evident to the casual observer have the effect of lightening the basic color very materially. The above refers to the upper and visible portions of the petals. As the narrower portions of the petals toward the point of attachment are reached, the color becomes virtually white or white with a greenish cast. Ordinarily in a fully opened blossom there will be one or two points where this greenish color is slightly visible from the front view of the flower.

This new variety has a decided cinnamon scent, although not heavy or oppressive.

My new variety may also be described as somewhat resembling the well-known variety Mrs. C. W. Ward, but differing from it in many important particulars most apparent among which are the following;

1. The stems are heavier and the stems and leaves have a distinctive, fresh, bluish-green color in midwinter;
2. The flower is fuller and more nearly perfect in form;
3. The flower has more of a salmon color tone;
4. The calyx shows less tendency to split;
5. The new variety comes into flower more quickly and blooms more freely.

Having thus disclosed my invention, what I claim as new is:

The variety of fragrant, medium pink carnation herein illustrated and described, characterized particularly by its heavier stems and the distinctive blue-green color of its leaves and stems, its strong non-splitting calyx, its fuller flowers of the color shades described, and its habit of producing more flowers and in a shorter time after rooting than occurs in other somewhat similar medium pink varieties.

ADOLPHE FREDERICK JACOB BAUR.